US00PP15607P2

(12) United States Plant Patent
Sakazaki

(10) Patent No.: US PP15,607 P2
(45) Date of Patent: Mar. 1, 2005

(54) ***PETUNIA* PLANT NAMED 'USTUNI207'**

(50) Latin Name: *Petunia×hybrida*
Varietal Denomination: USTUNI207

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/827,544

(22) Filed: Apr. 19, 2004

(51) Int. Cl.[7] ..... A01H 5/00
(52) U.S. Cl. ..... Plt./356
(58) Field of Search ..... Plt./356

(56) References Cited

PUBLICATIONS

UPOV–Rom, GTI Jouve retrieval software, Plant Variety Database 2004/02, hit on 'USTUNI207'.*

* cited by examiner

*Primary Examiner*—Anne Marie Grunberg
(74) *Attorney, Agent, or Firm*—C. A. Whealy

(57) ABSTRACT

A new and distinct cultivar of *Petunia* plant named 'USTUNI207', characterized by its semi-upright to cascading plant habit; freely branching habit; numerous single flowers that are light purple in color with red purple-colored venation; and good garden performance.

1 Drawing Sheet

Botanical classification/cultivar designation: *Petunia×hybrida* cultivar USTUNI207.

BACKGROUND OF THE INVENTION

The present Invention relates to a new and distinct cultivar of *Petunia* plant, botanically known as *Petunia×hybrida,* and hereinafter referred to by the cultivar name USTUNI207.

The new *Petunia* is a product of a planned breeding program conducted by the Inventor in Hikone, Shiga, Japan. The objective of the breeding program is to create new disease-resistant and heat-tolerant *Petunias* with semi-upright plant habit and attractive flower colors.

The new *Petunia* originated from a cross-pollination made by the Inventor on May 6, 1998 of the *Petunia* cultivar Fantasy Blue, not patented, as the female, or seed parent, with an unnamed selection of *Petunia,* not patented, as the male, or pollen parent. The new *Petunia* was selected as a single plant from the resulting progeny on Jun. 15, 1999 in Gensingen, Germany, on the basis of its plant habit and attractive flower coloration.

Asexual reproduction of the new cultivar by terminal vegetative cuttings since Jun. 25, 1999, taken in Gensingen, Germany has shown that the unique features of this new *Petunia* are stable and reproduced true to type in successive generations.

SUMMARY OF THE INVENTION

Plants of the cultivar USTUNI207 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USTUNI207'. These characteristics in combination distinguish 'USTUNI207' as a new and distinct cultivar:

1. Semi-upright to cascading plant habit.
2. Freely branching habit.
3. Numerous single flowers that are light purple in color with red purple-colored venation.
4. Good garden performance.

In side-by-side comparisons conducted in Hikone, Shiga, Japan, plants of the new *Petunia* differed from plants of the female parent, the cultivar Fantasy Blue, in the following characteristics:

1. Plants of the new *Petunia* were more cascading than and not as upright as plants of the cultivar Fantasy Blue.
2. Plants of the new *Petunia* were more vigorous than plants of the cultivar Fantasy Blue.

In side-by-side comparisons conducted in Hikone, Shiga, Japan, plants of the new *Petunia* flowered earlier than plants of the male parent selection.

Plants of the new *Petunia* can be compared to plants of the cultivar Cascadia Pink Spark, not patented. In side-by-side comparisons conducted in Gensingen, Germany, plants of the new *Petunia* were more freely branching and more rain tolerant than plants of the cultivar Cascadia Pink Spark.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical plant of 'USTUNI207' grown in a container.

The photograph at the bottom of the sheet is a close-up view of typical flowers and leaves of 'USTUNI207'.

DETAILED BOTANICAL DESCRIPTION

The aforementioned photographs and following observations and measurements describe plants grown in Bonsall, Calif., in an outdoor nursery during the summer under full sun conditions with day temperatures ranging from about 18 to about 35° C. and night temperatures ranging from about 10 to about 21° C. After planting rooted cuttings, plants were grown for about eight weeks with three plants per 15-cm containers. Color references are made to The Royal Horticultural Society Colour Chart, 1995 Edition, except where general terms of ordinary dictionary significance are used.

Botanical classification: *Petunia×hybrida* cultivar USTUNI207.

Parentage:

*Female parent.*—*Petunia×hybrida* cultivar Fantasy Blue, not patented.

*Male parent.*—Unnamed selection of *Petunia×hybrida,* not patented.

Propagation:

*Time cutting.*—Terminal vegetative cuttings.

*Time to initiate roots, summer and winter.*—About 15 days at 20 to 22° C.

*Time to develop roots, summer and winter.*—About 20 days at 18 to 20° C.

*Root description.*—Fine; white, close to 155D, in color.

*Rooting habit.*—Freely branching.

Plant description:

*Form.*—Annual flowering plant; indeterminate; initially upright, then semi-upright to outwardly spreading and cascading; uniformly mounded plant form. Freely branching habit with about five main branches per plant each with multiple secondary branches. Pinching enhances development of lateral branches.

*Usage.*—Appropriate for hanging baskets, window boxes, patio containers and landscape applications.

*Plant height.*—About 14 cm.

*Plant diameter* (*area of spread*), *single plant.*—About 18 cm.

*Vigor.*—Vigorous; moderately rapid growth rate.

*Lateral branches.*—Length: About 20 cm. Diameter: About 2.5 mm. Internode length: About 2 cm. Texture: Pubescent. Color: 143B.

*Foliage description.*—Arrangement: Alternate before flowering; opposite after flowers develop; simple. Length: About 4.2 cm. Width: About 2.5 cm. Shape: Elliptic to spatulate. Apex: Acute. Base: Attenuate. Margin: Entire. Texture, upper and lower surfaces: Pubescent; slightly coarse; glandular; slightly viscid. Venation pattern: Pinnate, arcuate. Color: Developing leaves, upper surface: 144A. Developing leaves, lower surface: 144B. Fully expanded leaves, upper surface: 146A. Fully expanded leaves, lower surface: 146B. Venation, upper surface: 145A. Venation, lower surface: 146C. Petiole length: About 1.3 cm. Petiole diameter: About 2 mm. Petiole texture, upper and lower surfaces: Pubescent; viscid. Petiole color: 146C.

Flower description:

*Flower type and habit.*—Single salverform flowers; flowers face mostly upward or outward; axillary. Freely flowering habit, about eight to eleven flower buds and open flowers per lateral branch.

*Natural flowering season.*—Long day responsive; long flowering period, spring until frost in the autumn; flowering continuous during this period. Plants start flowering about four to six weeks after planting rooted cuttings. Flowers persistent.

*Flower longevity on the plant.*—About seven to ten days.

*Fragrance.*—None detected.

*Flower size.*—Diameter: About 4.5 cm. Tube length: About 3.5 cm. Throat diameter, distal end: About 1 cm. Tube diameter, proximal end: About 3 mm.

*Flower buds.*—Length: About 3.5 cm. Diameter: About 6 mm. Shape: Elongated oblong with flared and ruffled apices. Color: 186C; venation, 186A.

*Petals.*—Quantity/arrangement: About five petals fused in a single whorl, funnelform. Length from throat: About 2 cm. Width: About 2.3 cm. Shape: Roughly fan-shaped to obovate. Apex: Rounded to slightly acute. Margin: Entire. Texture, upper and lower surfaces: Smooth, velvety. Color: When opening, upper surface: 75C. When opening, lower surface: 75D. Fully opened, upper surface: 75A; color becoming closer to 75D, towards the margins, 72B, with development. Fully opened, lower surface: 75D. Flower throat (inside): 77A. Flower tube (outside): 186D. Venation, upper petal surface: 74A. Venation, lower petal surface: 186A. Venation, throat: 79B. Venation, tube: 194A.

*Sepals.*—Arrangement/appearance: Single whorl of five sepals fused at base, star-shaped. Length: About 1.5 cm. Width: About 4 mm. Shape: Linear; recurved. Apex: Rounded to broadly acute. Margin: Entire. Texture, upper and lower surfaces: Pubescent. Color, upper surface: 146A. Color, lower surface: 146B.

*Peduncles.*—Length: About 3.5 cm. Width: About 1 mm. Angle: About 45° from the stem. Strength: Strong. Texture: Pubescent. Color: 144A.

*Reproductive organs.*—Stamens: Quantity per flower: Five. Anther shape: Ovoid. Anther size: About 1.5 mm by 2 mm. Anther color: 91A. Pollen amount: Scarce. Pollen color: 202A. Pistils: Quantity per flower: One. Pistil length: About 1.8 cm. Style length: About 1.5 cm. Style color: 145C. Stigma shape: Rounded. Stigma color: 148A. Ovary color: 145B.

*Seed/fruit.*—Seed and/or fruit production has not been observed.

Disease/pest resistance: Plants of the new *Petunia* have not been noted to be resistant to pathogens or pests common to *Petunia.*

Garden performance: Plants of the new *Petunia* have been observed to have good garden performance. Plants of the new *Petunia* have been noted to tolerate temperatures from 0 to 38° C. and have excellent tolerance to rain and wind.

It is claimed:

1. A new and distinct cultivar of *Petunia* plant named 'USTUNI207', as illustrated and described.

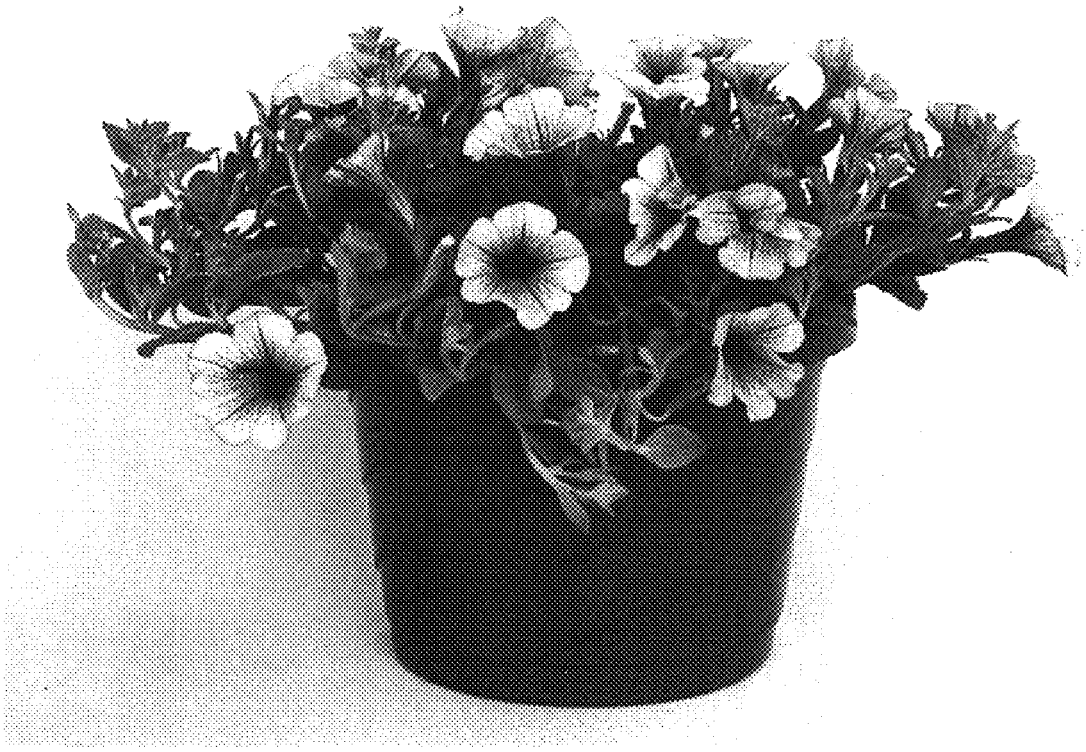
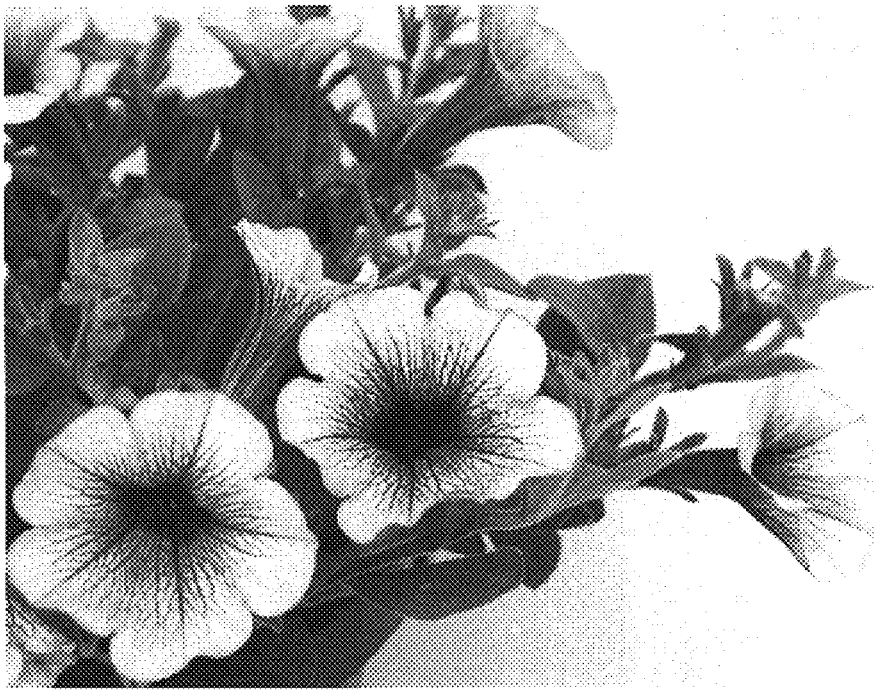

* * * * *